United States Patent [19]

Chudyk et al.

[11] Patent Number: 4,782,234
[45] Date of Patent: Nov. 1, 1988

[54] METHOD AND APPARATUS FOR SUBSURFACE CONTAMINANT DETECTION AND MEASUREMENT

[75] Inventors: Wayne A. Chudyk; Jonathan E. Kenny, both of Somerville, Mass.

[73] Assignee: Tufts University, Medford, Mass.

[21] Appl. No.: 737,191

[22] Filed: May 23, 1985

[51] Int. Cl.⁴ .............................................. G01J 1/58
[52] U.S. Cl. .................................. 250/372; 250/253; 250/461.1
[58] Field of Search .................... 250/461.1, 253, 372; 350/96.15, 96.29; 128/633, 634

[56] References Cited

U.S. PATENT DOCUMENTS

| | | | |
|---|---|---|---|
| 4,178,512 | 12/1979 | Früngel et al. | 250/253 |
| 4,186,303 | 1/1980 | Smith et al. | 250/253 |
| 4,344,438 | 8/1982 | Schultz | 128/634 |
| 4,403,826 | 9/1983 | Presby | 250/372 |
| 4,473,599 | 9/1984 | Elion | 350/96.29 |
| 4,504,114 | 3/1985 | Arrington | 350/96.29 |
| 4,577,109 | 3/1986 | Hirschfeld | 250/461.1 |
| 4,608,990 | 9/1986 | Elings | 128/633 |
| 4,623,789 | 11/1986 | Ikeda et al. | 128/634 |

Primary Examiner—Janice A. Howell
Assistant Examiner—David P. Porta
Attorney, Agent, or Firm—Cesari and McKenna

[57] ABSTRACT

Subsurface contaminants are readily and inexpensively detected and measured by means of a test head positioned at the subsurface site and forming a protected test chamber for the liquids to be tested. The head encloses the end faces of fiber optic elements which carry radiation to the liquid sample from a test instrument located at the surface and which return radiation from the sample to the instrumentation. A connector positioned at the surface decouples the head from the instrumentation, so that the same instrumentation can service a larger number of test sites.

11 Claims, 2 Drawing Sheets

METHOD AND APPARATUS FOR SUBSURFACE CONTAMINANT DETECTION AND MEASUREMENT

BACKGROUND OF THE INVENTION

A. Field of the Invention

The invention relates to contaminant detection and measurement and, more particularly, to subsurface contaminant detection and measurement.

B. Prior Art

The detection and measurement of subsurface contaminants is a key factor in efforts to maintain and improve the quality of the environment. This is particularly the case with respect to drinking water, which is highly susceptible to contamination during its passage through underground streams in the water cycle.

Conventional methods for monitoring subsurface liquid contaminants include both periodic sampling, with subsequent field or laboratory analysis, and in situ measurement. The former provides a reasonable measure of contamination for many purposes, but is often unsuited to precise measurement of contaminants which may be present in low concentrations (parts per million or less) since the sampling process itself disturbs the sample and may in fact alter the concentration of the constituents of interest. The latter method provides a means of avoiding this disturbance, but requires positioning a sensor containing sensitive equipment in an environment that is frequently hostile to the longevity of the sensor and its associated elements. Further, the sensor and its related equipment are typically quite expensive, and the number of sites that can practically be monitored is correspondingly limited.

Fiber optic signal transmission systems are being used in many applications where information must be transmitted from a remote site, including ground water measurement systems. See Hirschfeld et. al., Optical Engineering, vol. 22, no.5 pp. 527–531 (1983). Such systems typically irradiate a sample with an optical signal, and transmit the resultant return signal down the cable for analysis at a remote location. This allows removal of many of the sensitive elements of the sensor from the sensor head, and thereby contributes to the longevity of the system. However, the head itself is still subject to contamination from its environment, and this can affect not only its practical life but also the quality of the measurements.

BRIEF SUMMARY OF THE INVENTION

A. Objects of the Invention

Accordingly, it is an object of the invention to provide an improved method and apparatus for subsurface contaminant detection and measurement.

Further, it is an object of the invention to provide a method and apparatus for subsurface contaminant detection and measurement that facilitates economical monitoring of a large number of subsurface sites.

Yet a further object of the invention is to provide a method and apparatus for subsurface detection and measurement that ppovides an extended life to the measuring apparatus.

B. Brief Summary of the Invention

In accordance with the present invention, a measurement system is formed from an instrument station detachably coupled through a fiber optic link to a test head for positioning at a remote site. The test head comprises an elongated body defining and enclosing a chamber therein for receiving a liquid which is to be analyzed. The liquid is admitted to the chamber through a porous screen which blocks from entrance to the chamber solids and other large-size contaminants which can interfere with the measurement. In an actual embodiment of the invention described herein, the screen comprises a microporous wall forming part of the body itself and defining the chamber.

The head encloses the active end of one or more optical fibers and secures the end in predefined relation to the chamber and thus to the liquid sample therein. The remote end of the fiber(s) is secured to a connector which detachably mates with a corresponding connector associated with remote instrumentation which receives the signal from the head via the fiber optic cable and anaylzes, records, or otherwise processes the received signal.

In use, the head is positioned at the site at which monitoring is to occur; for example, at the bottom of a bore-hole leading into a water table. Because of the small size to which the head construction lends itself, such bore holes may be quite narrow (e.g. less than an inch in diameter) and thus inexpensively formed. Further, because of the simplicity of design which results in low fabrication costs, the head may be left permanently in place. In such a case, the bore hole may sealed, with only the connector (and perhaps a protective cover) extending beyond the hole for engagement with the instrumentation coupler. A large number of such test sites can thereby economically be established, and serviced from a single instrumentation station which is successively connected to each of the connectors in turn to monitor the water quality at the respective locations.

DETAILED DESCRIPTION OF THE INVENTION

The foregoing and other and further objects of the invention will be more readily understood from the following detailed description of the invention, when taken in conjunction with the accompanying drawings, in which.

Figure 1:
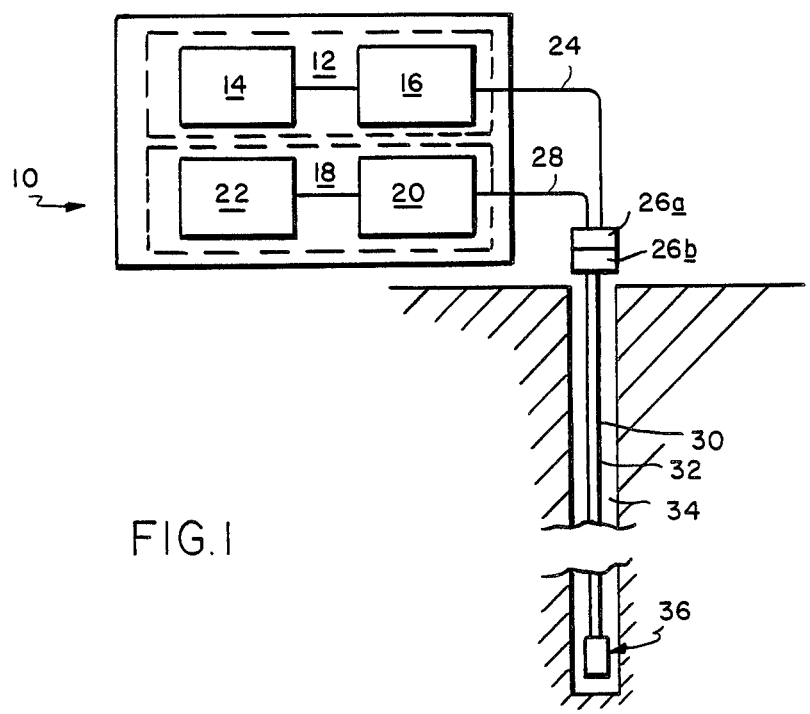
FIG. 1 is an illustrative sketch of an instrumentation station and test head in accordance with the present invention.

In FIG. 1, an instrument station 10 includes a signal source 12 comprising, for example, a source 14 of optical radiation, together with a filtering and selection element 16, and a signal receiver 18 comprising, for example, a radiation detector 20, and a radiation analyzer 22. The source 12 is connected via a fiber optic cable 24 to a first portion 26a of a connector 26, while the receiver 18 is connected to the portion 26a via a fiber optic cable 28. A mating lower portion 26b of connector 26 has connected therto fiber optic cables 30 and 32 which extend downwardly within a bore hole 34 to a test head 36 at the bottom of the bore hole.

Figure 2:
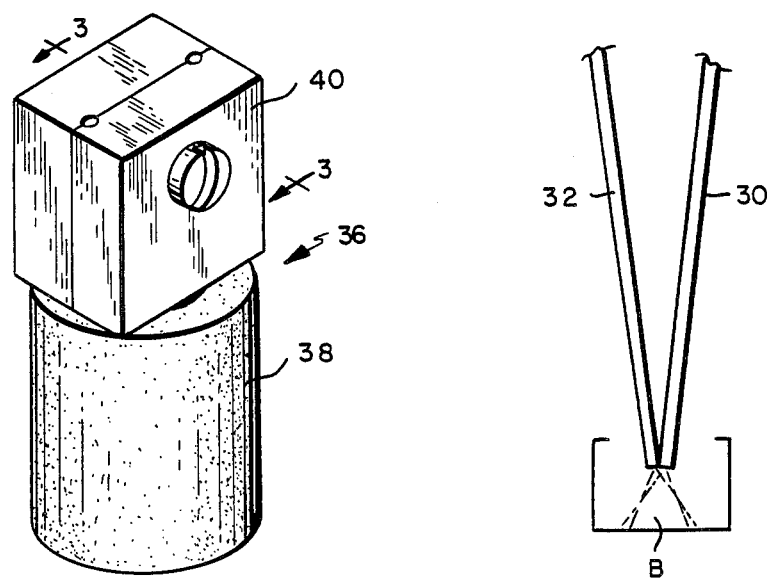
FIG. 2 is a view in perspective of the test head of FIG. 1.
Figure 3:
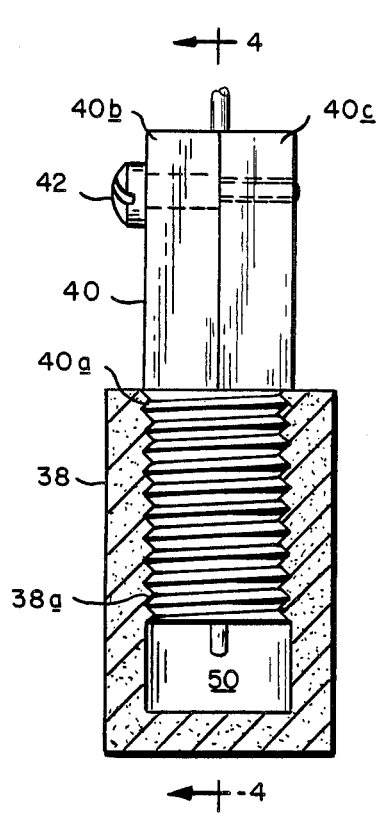
FIG. 3 is side sectional view of the tes head taken along the lines 3—3 of FIG. 2.
Figure 4:
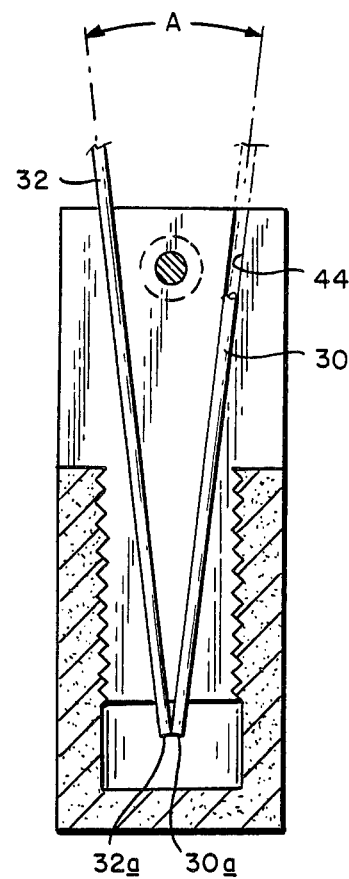
FIG. 4 is sectional view of the test head taken along the lines 4—4 of FIG. 3.

The head 36, shown in more detail in FIGS. 2-4, comprises a cylindrical body 38 and a cap 40. The interior of the body is threaded at its upper portion 38a to receive a correspondingly threaded lower portion 40a of cap 40. The cap 40 is formed of mating first and second segments 40b and 40c, respectively. A set screw 42 secures the two segments togther. Grooves 44 formed on the interior walls of one of the segments (only one such groove is shown in FIG. 4) carry the fiber optic cables 30, 32. These cables are secured by the cap to meet at an angle A as shown in FIG. 4.

The lower portion of the cap 40 forms, with the lower portion of the body 38, a chamber 50 for receiving liquid to be tested. In the specific device illustrated herein, the liquid is admitted to the chamber through the walls of the body 38. For this purpose, the body 38 is formed from a sintered metal such as stainless steel having a pore size which screens out particles greater than on the order of 30 microns in diameter. Thus, the head may be positioned in an otherwise hostile environment, but the chamber will nontheless be protected against contaminants which might interfere with the measurement.

Figure 5:
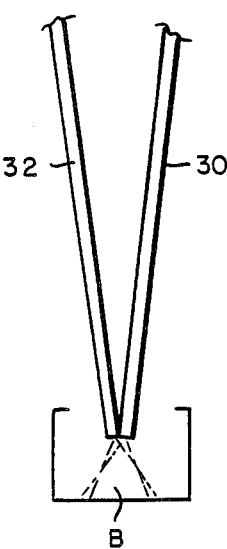
FIG. 5 is a sketch of the chamber of the test head showing the overlap of the incident and return radiation.

The manner in which the ends of the optical fiber are held in the test head contributes to the efficiency and efficacy of the measurement. In particular, the angle A (FIG. 4) between the fibers is on the order of from 15 to 25 degrees, preferably approximately 20 degrees. Further, the end faces 30a, 32a of the fibers 30, 32 are immediately adjacent each other, as shown in FIGS. 4 and 5. Thus, there is a substantial overlap (identified by the area B in FIG. 5) in the conical radiation and detection patterns of the fibers, and the level of the returned radiation is thereby enhanced.

The size of the head can be quite small. In a device built in accordance with the invention, the body was 1 inch long, and ½ inch in diamaeter. The cap was also 1 inch long, with a threaded portion of ½ inch so that, when asembled with the body, the overall length of the head was 1 ½ inches. and its diameter ½ inch. Thus, it is readily fitted in narrow test holes.

For monitoring water contaminants such as phenol, ortho-cresol, and humic acid, which are of particular concern in water quality monitoring, we have used, as the radiation source, a pulsed laser source operating in the ultraviolet region, specifically, at 266 nm. At this wavelength, the radiation incident on the sample causes fluorescence of sufficient intensity as to be allow detection of the presence of the above contaminants in amounts as low as parts per billion. The radiation was transmitted to the test head, and thus the sample, by optical fibers of approximately 1 mm in diameter and formed of fused silica with a Teflon coated body. These fibers are of narrow enough diameter to be sufficiently flexible so as to be of practical use in non-laboratory environments, yet do not excessively attenuate the transmitted and the returned radiation. With such fibers, and with the excitation source described above, distances of the order of 25 meters between the test head and the instrumetn stand are practical. Thus, contaminaton can be monitored at relatively deep sites.

The present invention allows permanent implantation of the test heads at numerous scattered sites which might generally be inappropriate as a practical matter for monitoring systems of larger size or cost. Further, because the heads can be permanently implanted at the site and decoupled from the measuring and analysis instrumentation, the cost of the monitoring is greatly reduced, and more extensive monitoring is therefor practicable, since a single instrumentation station 10 can serve an indefinite number of monitoring sites. Thus, closer monitoring of water quality can be obtained at reasonable cost.

It will be understoood that various changes can be made to the foregoing, without departing from either the spirit or the scope thereof. Thus, in some instances, a single fiber can be made to serve for transmitting both the stimulating and the return radiation. Further, the wavelength of the stimulating radiation may be varied in order to enhance detection of different constituents. Other changes of similar nature will suggest themselves to those skilled in the art.

What is claimed as new and desired to be secured by Letters Patent of the United States is:

1. A test head for detecting contaminants by means of optical radiation emitted from a sample, comprising:
   A. a channeled body for receiving and orienting in first and second channels thereof, respectively, a first fiber for reradiating a sample with fluorescence-inducing radiation transmitted through said fiber, and a second fiber for receiving fluorescent radiation emitted from said sample in response to irradiation, said channels positioning corresponding ends of said fibers in predetermined angular orientation with respect to each other, said body comprising first and second shoulders mateable with each other to enclose said fibers therein, at least one of said shoulders having the first and second channels formed therein and said channels being oriented at an acute angle to each other to provide a substantial overlap of radiation patterns associated with each of said first and second fibers;
   B. means forming a filter enclosing at least said fiber ends and defining with said body an enclosed chamber exposed to said fiber ends for receiving by infiltration through said filter a liquid sample for irradiation by a first of said fibers and re-radiation to a second of said fibers; and
   C. means for demountably coupling said test head to a radiation source and to a radiation measuring station.

2. A test head for detecting contaminants by means of optical radiation emitted from a sample, comprising:
   A. a channeled body for receiving and orienting in first and second channels thereof, respectively, a first fiber for reradiating a sample with fluorescence-inducing radiation transmitted through said fiber, and a second fiber for receiving fluorescent radiation emitted from said sample in response to irradiation, said channels positioning corresponding ends of said fibers in predetermined angular orientation with respect to each other, said body comprising first and second shoulders mateable with each other to enclose said fibers therein, at least one of said shoulders having the first and second channels formed therein and said channels being oriented at an acute angle to each other;
   B. means forming a filter enclosing at least said fiber ends and defining with said body an enclosed chamber exposed to said fiber ends for receiving by infilatration through said filter a liquid sample for irradiation by a first of said fibers and re-radiation to a second of said fibers;
   C. means for dedemountably coupling said test head to a radiation source and to a radiation measuring station; and D. said shoulders including a threaded portion on one end thereof for engagement with a coresponding threaded portion of said filter means.

3. A test head according to claim 2 in which said channels are oriented to position said fibers at an acute angle with respect to each other for efficiently receiving radiation induced in said sample.

4. A test head according to claim 3 in which said fluorescence-inducing radiation lies in the ultraviolet region.

5. A test head according to claim 2 in which said filter is of sintered metal for simultanously providing filtering and structural intergrity.

6. Apparatus for monitoring subsurface liquids comprising:
   A. a cylindrical body having a threaded upper portion and a porous portion;
   B. cap means, having a threaded lower portion, first and second segments, and a first groove formed on one of the segments, for engaging the body to form a chamber therewith, and for accomodating and positioning a first fiber optic cable in a predetermined spatial orientation with respect to the chamber.

7. Apparatus as in claim 6 where the porous portion of the body is formed of sintered metal.

8. Apparatus as in claim 6 where the cap means additionally comprises a second groove, sized and positioned to accomodate a secodn fiber optic cable in a predetermined spatial orientation with respect to the first cable.

9. Apparatus as in claim 8 where the cap means additionally has the second groove positioned to enhance a returned level of conical radiation.

10. Apparatus as in claim 6 where the cap means additionally positions the end faces of the cables near a bottom of the chamber to limit a return radiation volume.

11. Apparatus as in claim 6 additionally comprising:
   D. means for demountably coupling the cables to a fluorescing radiation source and detector.

* * * * *